United States Patent [19]

Takahashi et al.

[11] Patent Number: 5,078,992

[45] Date of Patent: Jan. 7, 1992

[54] WATER-ABSORBING RESIN COMPOSITION CONTAINING METALLOPHTHALOCYANINE

[75] Inventors: Yoshiyuki Takahashi, Suita; Tadao Shimomura; Naoyuki Shirane, both of Toyonaka, all of Japan

[73] Assignees: Ahsu Kurin Kabushiki Kaisha, Ueda; Nisshin Seifun Kabushiki Kaisha, Tokyo; Nippon Shokubai Co., Ltd., Osaka, all of Japan

[21] Appl. No.: 489,098

[22] Filed: Mar. 6, 1990

[30] Foreign Application Priority Data

Mar. 8, 1989 [JP] Japan .................................. 1-55457

[51] Int. Cl.$^5$ .................................................. A61L 9/01
[52] U.S. Cl. ............................... 424/76.3; 424/76.2; 424/76.21; 424/76.5; 424/76.6; 424/76.7; 523/102
[58] Field of Search .................... 424/76.3, 76.2, 76.21, 424/76.5, 76.6, 76.7; 523/102

[56] References Cited

U.S. PATENT DOCUMENTS

| | | | |
|---|---|---|---|
| 2,789,078 | 4/1957 | Trusler | 424/76.5 |
| 3,725,311 | 4/1973 | Grubb | 424/76.21 |
| 4,256,597 | 3/1981 | Sakkab | 252/95 |

FOREIGN PATENT DOCUMENTS

| | | |
|---|---|---|
| 54-157834 | 12/1979 | Japan . |
| 61-258806 | 11/1986 | Japan . |
| 61-258815 | 11/1986 | Japan . |
| 62-97555 | 5/1987 | Japan . |

*Primary Examiner*—Ronald W. Griffin
*Attorney, Agent, or Firm*—Oblon, Spivak, McClelland, Maier & Neustadt

[57] ABSTRACT

Disclosed herein are a water-absorbing resin composition composed of a water-absorbing resin and a metallophthalocyanine, and a method for utilizing the water-absorbing resin composition as a deodorant in the presence of water.

8 Claims, No Drawings

WATER-ABSORBING RESIN COMPOSITION CONTAINING METALLOPHTHALOCYANINE

BACKGROUND OF THE INVENTION

1. Field of the Invention

The present invention relates to a water-absorbing resin composition containing a metallophthalocyanine, which exhibits the outstanding chemical activity particularly in the presence of water, and also to a method of utilizing said resin composition. The resin composition of the present invention is useful particularly as a deodorant. It will also find use in any other application areas where it is possible to utilize the chemical activity of metallophthalocyanines.

2. Description of the Prior Art

It is known that such metal complexes as metalloporphyrins and metalloporphyrazines have an oxidation-reduction power and hence an ability to decompose a variety of chemical substances by their catalytic action. In the case where the chemical substances are the components of an offensive odor, their ability produces a deodorizing effect through the decomposition of such components. Above all, metallophthalocyanines are considered to be promising as a deodorant and their usage is under study on account of their characteristic properties given below.

(1) Capable of decomposing smelly substances rapidly and efficiently.
(2) Capable of reactions at normal temperature.
(3) Capable of decomposition reactions in the presence of water.
(4) Capable of utilizing oxygen in the air for oxidative decomposition.
(5) Capable of cyclic reactions with a long catalyst life.

For practical use as a deodorant, a metallophthalocyanine is made water-soluble by the introduction of substituent groups into it (as proposed in Japanese Patent Publication No. 57063/1988), or thus prepared water-soluble metallophthalocyanine is bound to a polymeric compound such as polystyrene and polyvinyl alcohol, for convenient use in the form of fiber, film, or powder (as proposed in Japanese Patent Publication No. 11307/1989).

It should be noted that the above-mentioned metallophthalocyanine is effective as a catalyst for the decomposition of smelly substances only in the presence of water, and that it does not exhibit the satisfactory catalytic activity when the amount of water is insufficient. According to the conventional technology, therefore, it has been an important practice to supply water in some form to the reaction system in which a metallophthalocyanine is involved, thereby keeping it active. Nevertheless, no due attention has been paid to the specific means to supply water. There has been no adequate means to supply as much water as necessary in a stable manner over a long period of time. Therefore, it has been necessary to supply water frequently to maintain the desired activity, because the shortage of water supply reduces the activity and the water supplied evaporates constantly, resulting in the reduced activity. In other words, it is difficult to keep the activity of a metallophthalocyanine.

It is an object of the present invention to address the above-mentioned problem and hence to provide a means to supply water in a stable manner to a metallophthalocyanine, thereby keeping it active for a long period of time.

SUMMARY OF THE INVENTION

The above-mentioned object is achieved by a resin composition which is composed of a water-absorbing resin and a metallophthalocyanine as an active ingredient, said resin composition permitting the metallophthalocyanine to be active continuously in the presence of water. This resin composition extremely promotes the decomposition of smelly substances because it contains a metallophthalocyanine and water together. Therefore, it will find use in a broad range of application areas where deodorizing is required. The use of the present invention is not limited to deodorizing; but it also includes those areas in which a metallophthalocyanine exhibits its chemical activity in the presence of water.

DETAILED DESCRIPTION OF THE INVENTION

The metallophthalocyanine used in the present invention is represented by the following formula.

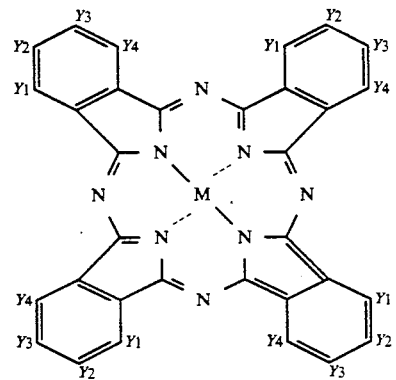

(where M denotes a metal atom; and one or more of $Y_1$–$Y_4$ are the same or different substituent groups, with the remainder being hydrogen atoms.)

The metal atom denoted by M in the above formula includes, for example, iron, cobalt, copper, nickel, manganese, osmium, titanium, molybdenum, and tungsten. Iron and cobalt produce the best deodorizing effect. The substituent groups denoted by $Y_1$–$Y_4$ include, for example, alkyl group, substituted alkyl group, aryl group, halogen, nitro group, amino group, substituted amino group, azo group, thiocyanate group, carboxyl group, chloroformyl group, aldehyde group, amide group, ester group, acyl group, nitrile group, hydroxyl group, alkoxyl group, aryloxy group, sulfonic group, sulfonylchloride group, sulfoneamide group, mercapto group, alkylmercapto group, alkyl silicon group, and vinyl group. The carboxyl group or sulfonic group may form a metal salt, and the amino group may form a quaternary salt.

The above-mentioned substituent groups are explained further below with reference to typical examples. The alkyl group is exemplified by lower alkyl groups such as methyl, ethyl, propyl, isopropyl, butyl, tertiary butyl, pentyl, and hexyl. The substituted alkyl group is exemplified by those groups formed by substituting the above-mentioned lower alkyl group with a halogen, nitro group, amino group, carboxyl group, aldehyde group, amide group, ester group, nitrile group, hydroxyl group, mercapto group, alkoxyl group, alkylmercapto group, or aryl group, in an arbitrary position. The aryl group is exemplified by phenyl and naphthyl. The substituted amino group is exemplified by a secondary or tertiary amino group substituted with an alkyl group or aryl group. The amide group is exemplified by a carbamoyl group and a carbamoyl group with an amino group therein substituted with an alkyl group or aryl group. The ester group is exemplified by a variety of acyloxy and carboalkoxy groups. The acyl group is exemplified by lower alkane carbonyl groups such as acetyl, propionyl, and butyryl, and aryl carbonyl such as benzene carbonyl and naphthalene carbonyl. The alkoxyl group is exemplified by lower alkoxyl groups such as methoxy, ethoxy, propoxy, butoxy, and tertiary butoxy. The aryloxy group is exemplified by phenoxy and naphthoxy. The alkylmercapto group is exemplified by lower alkylthio groups such as methylthio, ethylthio, and propylthio. The alkyl silicon is exemplified by lower alkyl silicon such as methyl silicon, ethyl silicon, and propyl silicon.

In addition, the above-mentioned substituent groups may be combined with an inorganic substance or polymeric compound. The inorganic substance includes, for example, silica gel, glass fiber, and carbon fiber; and the polymeric compound includes natural polymeric compounds and derivatives thereof such as cellulose, starch, gelatin, casein, and guaiac gum, and also includes synthetic polymeric compounds such as polyvinyl alcohol, poly(meth)acrylic acid and metal salts thereof or alkyl ester thereof, poly(meth)acrylamide, polymono- or polydialkylamino(meth)acrylate, polyhydroxyalkyl(meth)acrylate, polyvinylsulfonic acid and metal salts thereof, polyvinyl esters, polystyrene, polyvinyl acetal, polyester, polyamide, amino resin, alkyd resin, and copolymers thereof, which can combine with the above-mentioned substituent groups.

The water-absorbing resin used in the present invention is not specifically limited so long as it has an adequate degree of water absorption and water retention. It should be able to absorb more than twice as much water as the weight of its own (preferably 5-1000 times the weight of its own), so that it permits the metallophthalocyanine to fully exhibit its activity. Examples of such water-absorbing resins include cross-linked polyacrylate, acrylic acid-grafted starch, a neutralized product of cross-linked isobutylene maleic anhydride copolymer, and a saponified product of vinyl acetate-acrylate ester copolymer.

The water-absorbing resin may be incorporated with the metallophthalocyanine in any manner. The incorporation may be accomplished by for example, mixing the water-absorbing resin in powder form with the metallophthalocyanine by wet process; by mixing the water-absorbing resin in the form of water-containing gel as an intermediate with the metallophthalocyanine in powder form; and by polymerizing the water-absorbing resin in the presence of the metallophthalocyanine.

The ratio of the water-absorbing resin to the metallophthalocyanine may be established according to the degree of activity required. It is usually 100,000 to 1 or below, preferably 0.1-10,000 to 1. With a ratio exceeding 100,000 to 1, the resulting composition contains too small an amount of metallophthalocyanine to produce the deodorizing effect. In the contrary, with a ratio lower than 0.1 to 1, the resulting composition is of no practical use for economical reason and inability to supply sufficient water.

When used as a deodorant, the composition obtained as mentioned above possesses the following advantages over a metallophthalocyanine used alone.

(1) Improved deodorizing action and durability

A metallophthalocyanine produces its deodorizing action very effectively in the presence of water as mentioned above, and the water-absorbing resin absorbs moisture from air or water in contact with it and retains the absorbed water. When a metallophthalocyanine and a water-absorbing resin are combined together, the latter provides the former with water at all times, permitting the former to produce the deodorizing action for a long period of time. This feature is of practical importance, while a resin having no water-absorbing ability doesn't have this feature.

(2) Increased effective area for activity

A metallophthalocyanine powder incorporated into the water-absorbing resin is dispersed in a comparatively large volume. This gives a small amount of metallophthalocyanine powder more chances of coming into contact with a smelly gas, which leads to an increased deodorizing effect. Therefore, the composition obviates the need of using the expensive component in large quantities.

(3) Effect of the water-absorbing resin as an extender

A metallophthalocyanine powder is so fine and light that it scatters easily and poses a dust problem, making its handling difficult. This drawback is eliminated by compounding it with the water-absorbing resin. The resulting composition is easy and safe to handle.

There are no restrictions on the usage of the water-absorbing resin composition pertaining to the present invention. The composition may be used as such in the form of powder. The composition may also be formed into granules, pellets, or compressed moldings. Moreover, it may be sandwiched between layers of paper, nonwoven fabric, or cloth, or it may be impregnated into or attached to a moisture-permeable material such as paper, nonwoven fabric, cloth, and film, or it may be blended with rubber or plastics. The composition may also be mixed with any organic or inorganic extender, and the resulting mixture may be used in any form as mentioned above.

Incidentally, the water-absorbing resin composition of the present invention becomes active as soon as it absorbs moisture from air; however, it may be supplied with water when it is put to use.

As mentioned above, the water-absorbing resin composition of the present invention effectively deodorizes smelly substances present in the surroundings of our daily life. Since it functions as a catalyst for deodorizing, it is not consumed. Therefore, it retains its deodorizing action for a long period of time. In conclusion, it is a very useful deodorant.

EXAMPLES

Example 1

A water-absorbing resin composition (1) was prepared from the following two components by wet mixing at normal temperature.

500 g of water-absorbing resin ("Aquaric CA", cross-linked polyacrylate, made by Nippon Shokubai Kagaku Kogyo Co., Ltd.)

5 g of iron phthalocyanine octacarboxylic acid in powder form ("Earthclean", made by Nisshin Flour Milling Co., Ltd.)

Examples 2 and 3

Water-absorbing resin compositions (2) and (3) were prepared in the same manner as in Example 1 except that the iron phthalocyanine octacarboxylic acid was replaced by a metallophthalocyanine defined in Table 1.

TABLE 1

| Example No. | $Y_1$ | $Y_2$ | $Y_3$ | $Y_4$ | M |
|---|---|---|---|---|---|
| 2 | H | COOH | H | H | Fe |
| 3 | H | COOH | COOH | H | Co |

Example 4

A water-absorbing resin composition (4) was prepared in the same manner as in Example 1 except that the water-absorbing resin was replaced by a commercial water-absorbing resin (acrylic acid-grafted starch).

Example 5

A water-absorbing resin composition (5) was prepared in the same manner as in Example 1 except that the amount of the iron phthalocyanine octacarboxylic acid was changed to 50 g.

Comparative Example 1

The iron phthalocyanine octacarboxylic acid in power form was used as such as a deodorant sample.

Comparative Example 2

The water-absorbing resin ("Aquaric CA") used in Example 1 was used alone as a deodorant sample.

Comparative Example 3

A mixture of 5 g of iron phthalocyanine octacarboxylic acid in power form and 25 g of water was used as a deodorant sample.

Performance Test 1

Each of the deodorant samples prepared as mentioned above was weighed into a Petri dish (10 cm in diameter) in such an amount that the weighed sample contained 30 mg of the metallophthalocyanine. The samples of Examples 1 to 5 and Comparative Example 2 were given 100 ml of water so that they absorb water to become a gel. The Petri dish was placed in a 1-liter polypropylene container closed with a lid.

Into each container were introduced ethyl mercaptan and ammonia gas, respectively with the initial concentration being 7,000 ppm. Thirty minutes later, the amount of the remaining gases was measured by gas chromatography or by gastic reactotube method. The residue (%) of each smelly component was obtained. The results are shown in Table 2.

TABLE 2

| Designation of deodorant | Amount of resin*[1] | Amount of deodorant taken (mg) | Residue (%) of ethyl mercaptan | Residue (%) of ammonia gas |
|---|---|---|---|---|
| Composition (1) | 100 | 3,030 | undetectable | undetectable |
| Composition (2) | 100 | 3,030 | undetectable | undetectable |
| Composition (3) | 100 | 3,030 | undetectable | undetectable |
| Composition (4) | 100 | 3,030 | undetectable | undetectable |
| Composition (5) | 10 | 330 | undetectable | undetectable |
| Comparative Example 1 | 0*[2] | 30 | 90 | 75 |
| Comparative Example 2 | —*[3] | 3,000 | 100 | 40 |
| Comparative Example 3 | 0 | 180 | 5 | 35 |

*[1]Ratio (by weight) of water-absorbing resin to metallophthalocyanine.
*[2]Contains no resin.
*[3]Contains no metallophthalocyanine.

It is noted from Table 2 that the water-absorbing resin composition of the present invention produced the outstanding deodorizing effect on both ethyl mercaptan and ammonia gas.

Performance Test 2

Five grams each of the water-absorbing resin compositions (1) and (2) obtained in Examples 1 and 2, respectively, was placed in a plastics container (120 mL). In the container was placed 100 mL of urine collected from 15 adult males. Thirty minutes later, the container was examined for odor by 50 male panelists (23–49 years old) with reference to the control containing no deodorant. The results are shown in Table 3.

TABLE 3

| Deodorant | Number of panelists who noticed no smell | Number of panelists who noticed a weak smell | Number of panelists who noticed a strong smell |
|---|---|---|---|
| Composition (1) | 50 | 0 | 0 |
| Composition (2) | 48 | 2 | 0 |
| Without deodorant | 0 | 0 | 50 |

It is noted from Table 3 that the water-absorbing resin composition of the present invention produces an outstanding deodorizing effect for human urine.

Examples 6 and 7

Water-absorbing compositions (6) and (7) were prepared in the same manner as in Example 1 except that the amount of the iron phthalocyanine octacarboxylic acid (in powder form) was changed to 0.5 g and 0.25 g, respectively.

Performance Test 3

Three grams each of the water-absorbing resin compositions (1), (6), and (7) was placed in a 1.5-liter plastics container. To the container was added 300 g of water for the gelation of the resin composition.

Into each container was introduced hydrogen sulfide, with the initial concentration being 100 ppm. Sixty minutes later, the amount of remaining hydrogen sulfide was measured by the gastic reactotube method. The residue in percent was obtained. The results are shown in Table 4.

TABLE 4

| Deodorant | Amount of resin[*1] | Amount of deodorant taken (g) | Residue (%) of hydrogen sulfide |
|---|---|---|---|
| Composition (1) | 100 | 3 | undetectable |
| Composition (2) | 1000 | 3 | undetectable |
| Composition (3) | 2000 | 3 | 5 |

[*1] Ratio (by weight) of water-absorbing resin to metallophthalocyanine.

It is noted from Table 4 that the water-absorbing resin composition of the present invention produces a sufficient deodorizing effect even when the amount of resin is as large as 2000 parts by weight for 1 part by weight of the metallophthalocyanine. However, it is desirable that the amount of resin should be properly adjusted according to the deodorizing performance required.

Although the invention has been illustrated by the preceding examples, it is not to be construed as being limited to the materials employed therein, but rather the invention encompasses the generic area as hereinbefore disclosed.

What is claimed is:

1. A water-absorbing resin composition which comprises a water-absorbing resin and a metallophthalocyanine, said composition being intended for use in the presence of water.

2. A water-absorbing resin composition as claimed in claim 1, wherein the water-absorbing resin is one which absorbs 5-1000 times as much water as its own weight.

3. A water-absorbing resin composition as claimed in claim 2, wherein the water-absorbing resin is a cross-linked polyacrylate or acrylic acid-grafted starch.

4. A water-absorbing resin composition as claimed in any of claims 1 to 3, wherein the metallophthalocyanine is one which is represented by the formula below

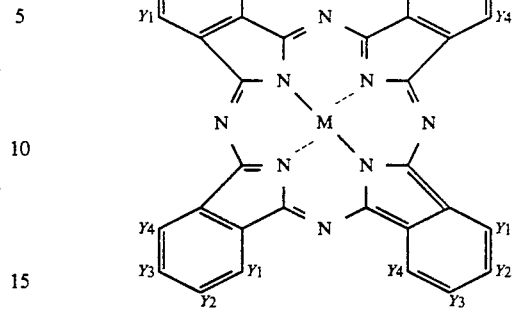

(where M denotes a metal atom; and one or more of $Y_1$-$Y_4$ are the same or different substituent groups selected from carboxyl group and sulfonic group, with the remainder being hydrogen atoms).

5. A deodorizing method which comprises using a water-absorbing resin composition composed of a water-absorbing resin and a metallophthalocyanine, in the presence of water.

6. A deodorizing method as claimed in claim 5, wherein the water-absorbing resin is one which absorbs 5-1000 times as much water as the weight of its own.

7. A deodorizing method as claimed in claim 6, wherein the water-absorbing resin is a cross-linked polyacrylate or acrylic acid-grafted starch.

8. A deodorizing method as claimed in claim 6, wherein the metallophthalocyanine is one which is represented by the formula below

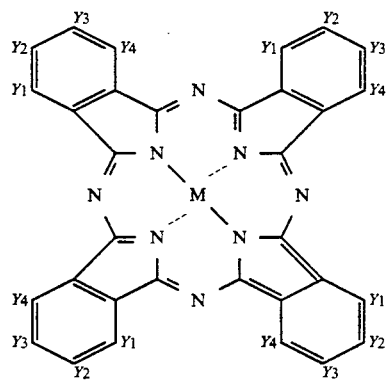

(where M denotes a metal atom; and one or more of $Y_1$-$Y_4$ are the same or different substituent groups selected from carboxyl group and sulfonic group, with the remainder being hydrogen atoms).

* * * * *